United States Patent [19]

Keller, Jr.

[11] 4,202,342
[45] May 13, 1980

[54] PROGRAMMABLE PACER WITH VARIABLE AMPLIFIER SENSITIVITY AND PACING RATE

[75] Inventor: John W. Keller, Jr., Miami, Fla.

[73] Assignee: Biotronik Mess- und Therapiegeräte GmbH & Co., Berlin, Fed. Rep. of Germany

[21] Appl. No.: 917,142

[22] Filed: Jun. 19, 1978

[30] Foreign Application Priority Data

Aug. 19, 1977 [GB] United Kingdom ............. 34917/77

[51] Int. Cl.² ............................................. A61N 1/36
[52] U.S. Cl. ........................................... 128/419 PG
[58] Field of Search ................... 128/419 PG, 419 PT

[56] References Cited

U.S. PATENT DOCUMENTS

| | | | |
|---|---|---|---|
| 3,805,796 | 4/1974 | Terry, Jr. et al. | 128/419 PG |
| 3,949,759 | 4/1976 | Brownlee et al. | 128/419 PG |
| 3,952,750 | 4/1976 | Mirowski et al. | 128/419 P |
| 4,049,004 | 9/1977 | Walter | 128/419 PG |

Primary Examiner—William E. Kamm
Attorney, Agent, or Firm—Spencer & Kaye

[57] ABSTRACT

An implanted receiver-decoder stores program bits corresponding to rate alteration and to input amplifier sensitivity. The former bits operate a rate decoder which in turn is responsive to predetermined outputs of a fixed rate oscillator-counter. The input amplifier is connected to the intermediate tap of a potential divider, one arm of which senses signals at the heart, and the other of which is either set at a fixed potential, or is allowed to float, under control of the input amplifier sensitivity programming signal.

2 Claims, 1 Drawing Figure

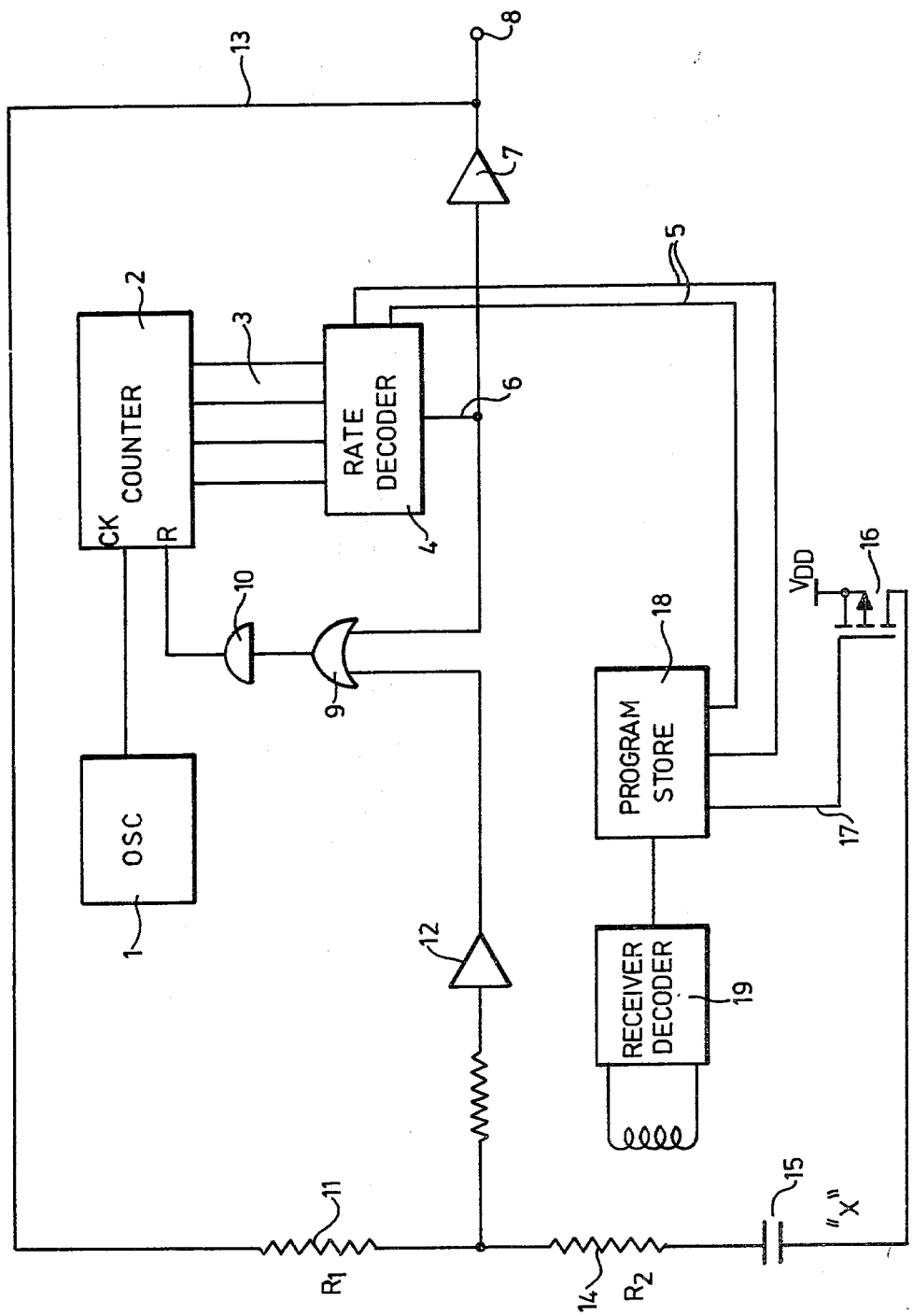

PROGRAMMABLE PACER WITH VARIABLE AMPLIFIER SENSITIVITY AND PACING RATE

FIELD OF THE INVENTION

This invention relates to implantable body function control apparatus and particularly, but not exclusively, to body tissue stimulating devices such as cardiac pacemakers.

BACKGROUND ART

Pacemakers for generating artificial stimulating pulses for the heart, and which may be implanted in the body, are well known. Originally the electrical circuitry for such pacemakers was of analog design, but in recent years digital circuitry has been also employed. A digital approach to pacemakers has led to the evolution of programmable pacemakers—pacemakers having parameters such as pulse rates which are adjustable (programmable) once the pacemaker has been implanted. The programs can be changed from outside the patient's body by appropriate signal transmission to the implanted pacemaker and without surgery. Programmable pacemakers are described in, for instance, British Patent Specifications Nos. 1,385,954 and 1,398,875. Such pacemakers have circuitry to detect and decode signals transmitted outside the body and alter the program accordingly. In British Patent Specificaton No. 1,385,954 the programming is accomplished by means of a magnetic field which is sensed by a magnetic reed switch; the opening and closing of the switch providing programming pulses to a program store. In British Patent Specification No. 1,398,875 the programming is by means of radio frequency transmission and reception.

Many pacemakers are of the demand type—that is they only supply a stimulating pulse to the heart when a natural heart beat is absent. To accomplish this, demand pacemakers have means for sensing the presence or absence of natural heart beats and for actuating the stimulating pulse as appropriate.

Demand pacemakers normally have an input amplifier which receives the electrical signals detected at the heart, and the amplified signals are then employed to control the demand function of the pacemaker. Generally, signals provided by the input amplifier are employed to inhibit any artificial pulse being generated by the pacemaker: the absence of such signals being taken by the pacemaker as indicating the absence of a normal heart beat and causing artificial stimulating pulses to be generated.

Pacemakers are implanted in the body for a period of years, and during that time various parameters can change causing the effective signals supplied by the input amplifier to change in magnitude. Typical of such parameters is an increase in impedance of the body tissue as "seen" by the pacing electrode. But most prevalent is the wide range of electrode placement effectiveness which can result in not only very large but very small signals.

DISCLOSURE OF THE INVENTION

We have now devised a pacemaker circuit which enables the signal magnitude supplied by the input amplifier to be changed without the need for removing the pacemaker from the recipient's body. This has been accomplished by providing different levels of attenuation for the output signal supplied by the input amplifier and by selecting the desired attenuation by means of a program held in a pacemeker program store.

According to the invention there is provided an implantable, body tissue stimulating apparatus comprising means for providing electrical signals for artificially stimulating body tissue in relation to sensed signals, said providing means including an input amplifier for receiving input signals from the body and for providing output signals for controlling the operation of the apparatus, means for controlling the magnitude of the output signals provided by the input amplifier, a program store for holding a program which controls said magnitude controlling means, and means for changing the program stored by the program store.

The magnitude control means can take several forms, but preferably includes a potential dividing network which by means of switching resistors into and out of the network, can be employed to control the signal levels at the input amplifier. This can be accomplished either on the input side of the amplifier (the input signals being supplied to the network before passing to the amplifier), by including the network in an amplifier feed-back loop (enabling the amplifier gain to be varied), or on the output side of the amplifier. Of these three alternatives, the first is preferred.

Although several levels of signal level attenuation are possible (and from which selection can be made), it has been found that two levels are sufficient in practice ("high" and "low"). Appropriate selection of one of these two levels can be accomplished simply by a single binary bit held in the program store.

BRIEF DESCRIPTION OF THE DRAWING

Preferred features of the invention are illustrated, by way of example, in the accompanying drawing which shows schematically an electrical circuit diagram of an implantable demand cardiac pacemaker according to the invention.

BEST MODE OF MAKING THE INVENTION

Referring to the drawing, the packmaker comprises an oscillator 1 which clocks a ripple counter 2. Various outputs from the ripple counter are combined as is known in the art by means of logic gates (not shown) to provide four output lines 3. The oscillator frequency and combination of ripple counter outputs are selected so that the four output lines 3 provide, respectively, body stimulation pulses at four different frequencies (e.g. 50, 60, 70, 80 pulses per minute). The four output lines 3 are supplied to a rate decoder 4 provided with two input control lines 5. By employing binary logic circuitry, the logic levels on lines 5 can be employed to select uniquely one from four of the four lines 3 and transmit the selected pulse frequency on line 6. Line 6 is connected to an output amplifier 7 which in turn is connected to a connection 8 which leads to an active stimulating pulse electrode (not shown) disposed in or on the heart. Line 6 also provides one input to an OR gate 9.

The output of OR gate 9 is supplied to a delay unit 10 whose output is employed to reset counter 2. The delay generated by delay unit 10 sets the pulse width for each artificial stimulating pulse which is transmitted on output line 6.

The active electrode disposed in or on the heart feeds back the electrical signals detected at the heart (arising from an artificial stimulating pulse or a natural heart beat) to the pacemaker via a resistor 11 ($R_1$). The output of resistor $R_1$ is connected to an input amplifier 12 which in turn supplies a second input to OR gate 9. The feedback loop for such signals through the active electrode is illustrated by means of line 13.

Connected to input amplifier 12 is a second resistor 14 ($R_2$), which is connected via a capacitor 15 to the drain of a field effect transistor 16, the source of which is connected to $V_{DD}$. The gate of the transistor 16 is controlled by a control line 17 which, as with control lines 5, extends from a pacemaker program store 18. The program store 18 is arranged to hold, as a pacemaker program, a series of binary values for supply on the control lines 5 and 17.

A receiver/decoder 19 is arranged to receive and decode data signals transmitted from outside the patient's body to the implanted pacemaker, and to employ the decoded signals for changing a pacemaker program held in program store 18. For the purposes of illustration, the receiver/decoder 19 and store 18 have been depicted simply in functional box-form. The data signals may be transmitted to the receiver/decoder 19 by any suitable means, but preferably we employ data signals transmitted by tone burst modulation (pulse width modulation of a carrier frequency). A receiver/decoder and program store for such data signals is described in copending application Ser. No. 917,130 filed on even date/(ref. DLD:10).

The pacemaker operates as follows. A program is entered and held in the program store 18 and the binary levels on control lines 5 determine which one of the four outputs 3 derived from counter 2 is passed by rate decoder 4 onto output line 6.

In the absence of natural heart beats, the counter 2 successively generates a series of artificial pulses at the selected rate and these are supplied to the heart via output amplifier 7. Each artificial pulse causes a reset of counter 2 via OR gate 9 and delay 10 to enable the count for the next artificial pulse to commence.

If a natural heart beat arises, an electrical signal is received by input amplifier 12 and counter 2 is reset (via OR gate 9 and delay 10) to inhibit any count in the process of being generated. Thus described, the pacemaker operates in a normal demand mode—issuing artificial pulses only when demanded by the heart. It is of no consequence if the reset initiated by a natural heart beat arrives just as an artificial pulse is generated, since the natural beat and the stimulating pulse will essentially coincide.

Should it be wished to vary the sensitivity of the input amplifier, then this may be accomplished as follows. If a "1" is held in program store 18 for output on line 17 ("1"=$V_{DD}$), then the gate voltage of transistor 16 equals $V_{DD}$ and maintains the latter non-conducting: the point "X" between capacitor 15 and transistor 16 drain "floats". In such a circumstance $R_2$ has no influence on the magnitude of the input signal to input amplifier 12, as applied through resistor $R_1$.

If a "0" is held in the program store 18 for output on line 17, transistor 16 conducts and this causes point "X" to be at $V_{DD}$. The result of this is to cause $R_1$ and $R_2$ to act as a potential divider for the input signal, causing the input signal to the input amplifier to be attenuated.

In the normal circumstances, a "0" is held in the program store 18 and this causes attenuation of the input signal to amplifier 12. The gain of amplifier 12 and other parameters of the circuit are set such that this attenuation is acceptable and that the attenuated signal received is still of sufficient magnitude to carry out its necessary function of controlling the demand function of the pacemaker.

Should it be desired to increase the input amplifier sensitivity (e.g. when there is an electrode displacement, or when the pacemaker batteries have suffered some loss of power after a relatively long period of use or when there is poor electrode placement, or the growth of tissue, all of which alter the signal "seen" by the pacemaker), then the program is changed to "1", to cause $R_2$ to float and remove attenuation of the input signal.

It will be appreciated that the circuit described above has been described in simple form, schematically, for the purposes of clarity. Also, though the amplifiers have been shown as single-input components it is of course possible to employ two input amplifiers (e.g. differential amplifiers).

What is claimed is:

1. In a programmable pacer system having a remote source of pacer function programming signals, an implantable cardiac pacer having programmably variable input amplifier sensitivity comprising:

pulse generating means for periodically issuing stimulating pulses;

an input amplifier for sensing signals at the heart and for resetting said generating means in response to a sensed signal, wherein the improvement comprises local memory means producing an output signal, responsive to signals from said remote source, a potential dividing network provided with an intermediate tap, means connecting said intermediate tap to the input of said amplifier, means connecting one extremity of said network to sense signals at the heart, and means connected to apply to the other extremity of said network a potential controlled by the output signal of said memory means for controlling the sensitivity of said input amplifier.

2. A pacer as described in claim 1 and wherein said means connected to apply a potential comprise:

a voltage source, a capacitor connected on one side to said other extremity of said network, and a switch means, between said source and the other side of said capacitor, said switch means being operated by the output signal of said memory means, thereby establishing control potentials at said other extremity and in turn varying the sensitivity of said amplifier.

* * * * *